United States Patent
Yang et al.

(10) Patent No.: US 11,427,639 B2
(45) Date of Patent: Aug. 30, 2022

(54) ANTIBODY-CONTAINING AQUEOUS FORMULATION AND USE THEREOF

(71) Applicant: RICHTER GEDEON NYRT., Budapest (HU)

(72) Inventors: Jheng-Gang Yang, Taichung (TW); Jiung-Liang Liu, Chayi County (TW); Wen-Cheng Chang, Taoyuan (TW)

(73) Assignee: Richter Gedeon Nyrt.

( * ) Notice: Subject to any disclaimer, the term of this patent is extended or adjusted under 35 U.S.C. 154(b) by 197 days.

(21) Appl. No.: 16/371,189

(22) Filed: Apr. 1, 2019

(65) Prior Publication Data
US 2019/0300615 A1 Oct. 3, 2019

Related U.S. Application Data

(60) Provisional application No. 62/651,269, filed on Apr. 2, 2018.

(51) Int. Cl.
| | |
|---|---|
| *C07K 16/28* | (2006.01) |
| *A61K 31/7016* | (2006.01) |
| *A61K 47/26* | (2006.01) |
| *A61P 37/00* | (2006.01) |
| *A61P 35/02* | (2006.01) |
| *A61P 19/02* | (2006.01) |
| *A61K 9/00* | (2006.01) |

(52) U.S. Cl.
CPC ........ *C07K 16/2866* (2013.01); *A61K 9/0019* (2013.01); *A61K 31/7016* (2013.01); *A61K 47/26* (2013.01); *A61P 19/02* (2018.01); *A61P 35/02* (2018.01); *A61P 37/00* (2018.01)

(58) Field of Classification Search
CPC .............. C07K 16/2866; A61K 9/0019; A61K 31/7016; A61K 47/26; A61P 37/00; A61P 19/02; A61P 35/02
See application file for complete search history.

(56) References Cited

U.S. PATENT DOCUMENTS 10,961,314 B2 * 3/2021 Del Rio ........... A61K 39/39591

OTHER PUBLICATIONS

Actemra® (Tocilizumab), Initial U.S. FDA Approval: 2010.*
Strickley et al., A review of formulations of commercially available antibodies. Journal of Pharmaceutical Science 110:2590-2608, 2021.*

* cited by examiner

Primary Examiner — Ruixiang Li
(74) Attorney, Agent, or Firm — McAndrews, Held & Malloy, Ltd.

(57) ABSTRACT

The present disclosure provides an antibody-containing aqueous formulation, comprising a therapeutically effective amount of an anti-interleukin-6 receptor antibody, a protein stabilizer, a surfactant, and a buffer. The buffer is an acetate buffer or a histidine buffer, and the antibody-containing aqueous formulation has a pH ranging from 4.5 to 6.5.

12 Claims, 3 Drawing Sheets

ANTIBODY-CONTAINING AQUEOUS FORMULATION AND USE THEREOF

CROSS-REFERENCE TO RELATED APPLICATION

The present disclosure claims priority to U.S. Provisional Application No. 62/651,269, filed on Apr. 2, 2018, the entirety of which is incorporated herein by reference.

FIELD OF THE DISCLOSURE

The present disclosure relates to an antibody-containing aqueous formulation, and more particularly, stabilizing interleukin-6 receptor antibodies in the antibody-containing aqueous formulation for treating interleukin-6-mediated diseases.

BACKGROUND OF THE DISCLOSURE

Interleukin-6 (IL-6) is a cytokine that is active in inflammation. IL-6 is involved in IL-6-mediated diseases, such as rheumatoid arthritis (RA) and systemic juvenile idiopathic arthritis. Hence, antibodies binding to IL-6 receptor are developed as the therapeutic agents for the IL-6-mediated diseases.

Tocilizumab IgG is a humanized monoclonal antibody against the IL-6 receptor. "Actemra®" manufactured by Chugai Pharmaceutical Co., Ltd. is a FDA-approved biologic containing Tocilizumab IgG. The intravenous formulation of Actemra® comprises 20 mg/ml of Tocilizumab IgG, 5% of sucrose, 0.05% of polysorbate 80, and 15 mM of sodium phosphate. The pH value of Actemra® intravenous formulation is 6.5.

However, Tocilizumab IgG formulated in Actemra® intravenous formulation is unstable when exposed to thermal stress. There is a 0.66% protein aggregation for Tocilizumab IgG in Actemra® intravenous formulation. After being subjected to 6 months of storage at 4° C. and 25° C., there are about 0.77% and 0.89% Tocilizumab IgG aggregations formed in Actemra® formulation. The protein aggregates formed in the formulation might induce immune response after being introduced into the human body. Therefore, there is a need to provide a more stable aqueous formulation that stabilizes Tocilizumab IgG and suppresses the aggregate formation of Tocilizumab IgG.

BRIEF SUMMARY OF THE DISCLOSURE

An objective of the present disclosure is to reduce aggregate formation of anti-interleukin-6 receptor antibody and retain at least 90% of monomer form of the anti-interleukin-6 receptor antibody.

Another objective of the present disclosure is to provide a stable aqueous formulation comprising Tocilizumab IgG used for intravenous administration.

An embodiment of the present disclosure provides an antibody-containing aqueous formulation. The antibody-containing aqueous formulation comprises a therapeutically effective amount of an anti-interleukin-6 receptor antibody, a protein stabilizer, a surfactant, and a buffer. The buffer is an acetate buffer or a histidine buffer, and the antibody-containing aqueous formulation falling within a pH of 4.5 to 6.5.

Preferably, the anti-interleukin-6 receptor antibody is Tocilizumab IgG.

Preferably, a concentration of the Tocilizumab IgG falls within a range of 5 mg/ml to 30 mg/ml.

Preferably, a concentration of the Tocilizumab IgG is 20 mg/ml.

Preferably, the protein stabilizer is sucrose or trehalose, and a concentration of the protein stabilizer falls within a range of 1% (w/v) to 10% (w/v).

Preferably, a concentration of the protein stabilizer is 7% (w/v).

Preferably, the surfactant is polysorbate 80, polysorbate 20 or poloxamer, and a concentration of the surfactant falls within a range of 0.01% (w/v) to 0.05% (w/v).

Preferably, a concentration of the surfactant is 0.03% (w/v).

Preferably, a concentration of the buffer falls within a range of 10 mM to 30 mM.

Preferably, a concentration of the buffer is 20 mM.

Preferably, the buffer is an acetate buffer, and a pH of the antibody-containing aqueous formulation falls within a range of 5.0 to 6.0.

Preferably, the buffer is a histidine buffer, and a pH of the antibody-containing aqueous formulation falls within a range of 5.5 to 6.5.

Preferably, the antibody-containing aqueous formulation comprises a tonicifer.

Preferably, the tonicifier is 0% (w/v) to 6% (w/v) of sorbitol. More preferably, the tonicifier is 1% (w/v) to 4% (w/v) of sorbitol.

Preferably, the anti-interleukin-6 receptor antibody is 5 mg/ml to 30 mg/ml of Tocilizumab IgG, the protein stabilizer is 4% (w/v) to 7% (w/v) of sucrose, the surfactant is 0.01% (w/v) to 0.05% (w/v) of polysorbate 80, the buffer is 10 mIVI to 30 mM of acetate buffer, and the antibody-containing aqueous formulation has a pH ranging between 5.0 and 6.0.

Preferably, the anti-interleukin-6 receptor antibody is 20 mg/ml of Tocilizumab IgG, the protein stabilizer is 7% (w/v) of sucrose, the surfactant is 0.03% (w/v) of polysorbate 80, the buffer is 20 mM of acetate buffer, and the antibody-containing aqueous formulation has a pH ranging between 5.0 and 5.5

Preferably, the anti-interleukin-6 receptor antibody is 5 mg/ml to 30 mg/ml of Tocilizumab IgG, the protein stabilizer is 4% (w/v) to 7% (w/v) of sucrose, the surfactant is 0.01% (w/v) to 0.05% (w/v) of polysorbate 80, the buffer is 10 mM to 30 mM of histidine buffer, and the antibody-containing aqueous formulation has a pH ranging between 5.5 and 6.5.

Preferably, the anti-interleukin-6 receptor antibody is 20 mg/ml of Tocilizumab IgG, the protein stabilizer is 7% (w/v) of sucrose, the surfactant is 0.03% (w/v) of polysorbate 80, the buffer is 20 mM of histidine buffer, and the antibody-containing aqueous formulation has a pH ranging between 5.5 and 6.5.

Preferably, the antibody-containing aqueous formulation comprises a tonicifier, and the tonicifier is 0% (w/v) to 6% (w/v) of sorbitol. More preferably, the tonicifier is 1% (w/v) to 4% (w/v) of sorbitol.

Preferably, the antibody-containing aqueous formulation forms less than 5% of aggregates of the anti-interleukin-6 receptor antibody after 3 months of storage at 40° C.

Preferably, at least 90% of the anti-interleukin-6 receptor antibody in the antibody-containing aqueous formulation is in monomer form after 3 months of storage at 40° C.

Preferably, the antibody-containing aqueous formulation forms less than 5% of aggregates, and at least 90% of the anti-interleukin-6 receptor antibody in the antibody-containing aqueous formulation is in monomer form after 3 months of storage at 40° C.

Another embodiment of the present disclosure provides a method of treating an interleukin-6-mediated disease. The method comprises administering the antibody-containing aqueous formulation to a mammalian body.

Another embodiment of the present disclosure provides a method of stabilizing anti-interleukin-6 receptor antibodies. The method comprises steps of formulating aforementioned antibody-containing aqueous solution.

Another embodiment of the present disclosure provides a method of suppressing aggregate formation of the anti-interleukin-6 receptor antibodies in an antibody-containing aqueous formulation. The method comprises steps of formulating aforementioned antibody-containing aqueous solution.

Preferably, the antibody-containing aqueous formulation is administered by intravenous injection or infusion.

Preferably, the interleukin-6-mediated disease is rheumatoid arthritis, systemic juvenile idiopathic arthritis, polyarticular juvenile idiopathic arthritis, Still's disease, Castleman's disease, giant cell arteritis, system sclerosis, cytokine release syndrome, polymyositis, dermatomyositis, familial mediterranean fever, polymyalgia rheumatic, Schnitzler syndrome, pulmonary arterial hypertension, pain, or B-cell chronic lymphocytic leukemia.

Another embodiment of the present disclosure provides a use of the aforementioned antibody-containing aqueous formulation in the manufacture of a medicament for treatment of an interleukin-6-mediated disease.

Preferably, the antibody-containing aqueous formulation is administered by intravenous injection or infusion.

Preferably, the interleukin-6-mediated disease is rheumatoid arthritis, systemic juvenile idiopathic arthritis, polyarticular juvenile idiopathic arthritis, Still's disease, Castleman's disease, giant cell arteritis, system sclerosis, cytokine release syndrome, polymyositis, dermatomyositis, familial mediterranean fever, polymyalgia rheumatic, Schnitzler syndrome, pulmonary arterial hypertension, pain, or B-cell chronic lymphocytic leukemia.

Another embodiment of the present disclosure provides a pharmaceutical composition for treatment of an interleukin-6-mediated disease. The pharmaceutical composition comprises the aforementioned antibody-containing aqueous formulation.

Preferably, the antibody-containing aqueous formulation is administered to a mammalian body by intravenous injection or infusion.

Preferably, the interleukin-6-mediated disease is rheumatoid arthritis, systemic juvenile idiopathic arthritis, polyarticular juvenile idiopathic arthritis, Still's disease, Castleman's disease, giant cell arteritis, system sclerosis, cytokine release syndrome, polymyositis, dermatomyositis, familial mediterranean fever, polymyalgia rheumatic, Schnitzler syndrome, pulmonary arterial hypertension, pain, or B-cell chronic lymphocytic leukemia.

In sum, according to various embodiments of the present disclosure, the antibody-containing aqueous formulation having a pH ranging between 4.5 and 6.5 can stabilize and reduce aggregate formation of the anti-Interleukin-6 receptor antibody in the antibody-containing aqueous formulation.

BRIEF DESCRIPTION OF THE DRAWINGS

The accompanying drawings illustrate one or more embodiments of the present invention and, together with the written description, explain the principles of the present disclosure. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
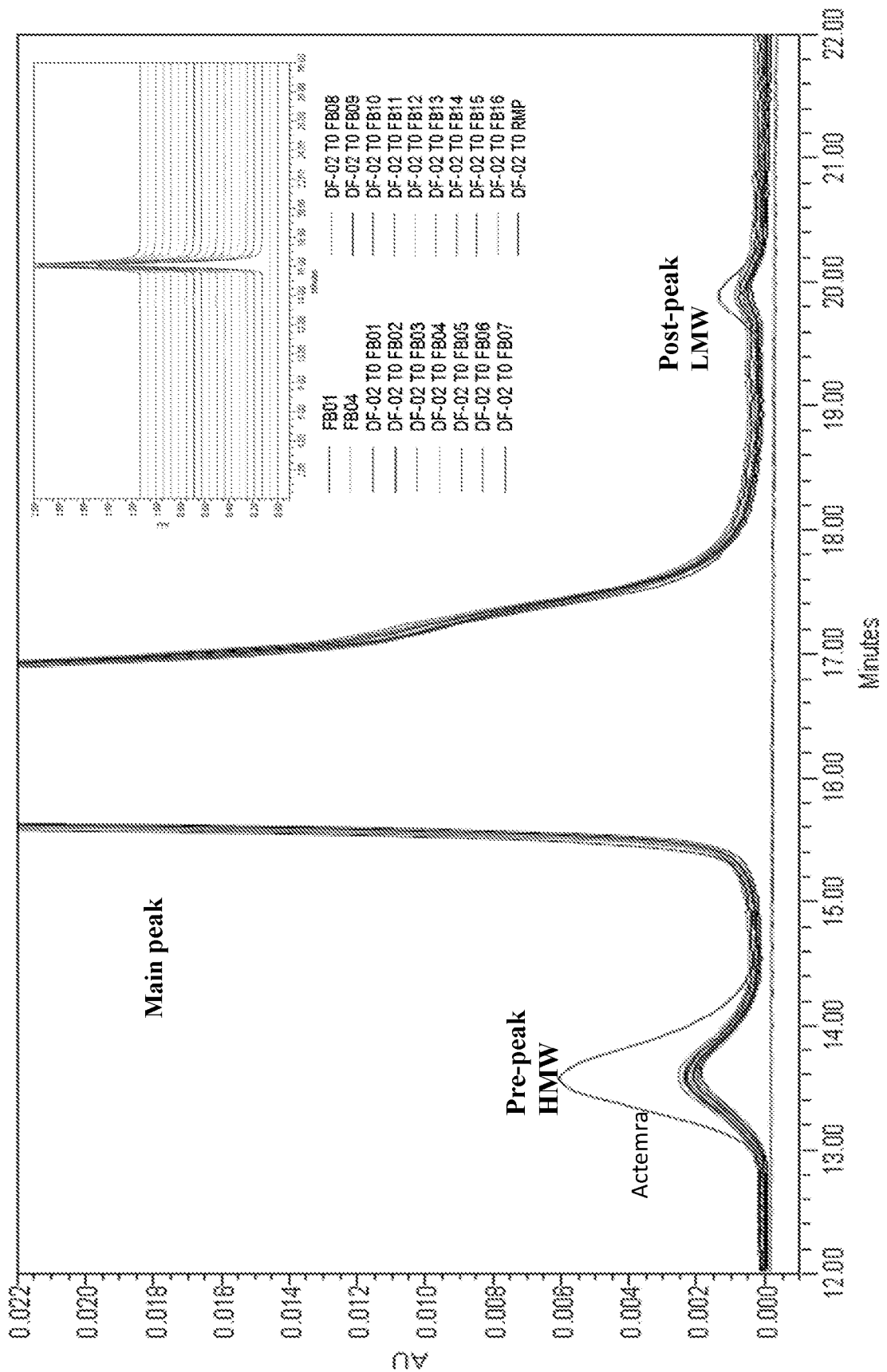
FIG. 1 is a SEC-HPLC profile of Tocilizumab IgG before being subjected to storage (To), according to an exemplary embodiment of the present disclosure.

The present disclosure will now be described more fully hereinafter with reference to the accompanying drawings illustrating various exemplary embodiments of the present disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

A "therapeutically effective amount" refers to an amount effective, at dosages and for periods of time necessary, to achieve the desired therapeutic result, such as suppression or inhibition of an interleukin-6-mediated disease. A therapeutically effective amount of an anti-interleukin-6 receptor antibody, may vary according to factors such as the disease state, age, gender, and weight of the subject, and the ability of anti-interleukin-6 receptor antibody, to elicit a desired response in the subject. Dosage regimens may be adjusted to provide the optimum therapeutic response. A therapeutically effective amount is also one in which any toxic or detrimental effects of anti-interleukin-6 receptor antibody are outweighed by the therapeutically beneficial effects.

A "prophylactically effective amount" refers to an amount effective, at dosages and for periods of time necessary, to achieve the desired prophylactic result, such as preventing an interleukin-6-mediated disease. A prophylactically effective amount can be determined as described above for the therapeutically effective amount. Typically, since a prophylactic dose is used in subjects prior to or at an earlier stage of disease, the prophylactically effective amount shall be less than the therapeutically effective amount.

It is to be noted that dosages of the anti-interleukin-6 receptor antibody may vary with the severity of the condition to be alleviated. It is to be further understood that for any particular subject, specific dosage regimens should be adjusted over time according to the individual need and the professional judgment of the person administering or supervising the administration of the immunotherapeutic combination.

In an embodiment of the present disclosure, an antibody-containing aqueous formulation includes the therapeutically effective or the prophylactically effective amount of the anti-interleukin-6 receptor antibody, a protein stabilizer, a surfactant, and a buffer. The antibody-containing aqueous formulation of the present disclosure has a pH of 4.5 to 6.5, and the buffer is acetate buffer or histidine buffer. The antibody-containing aqueous formulation of the present disclosure can cause less than 5% aggregate formation of the anti-interleukin-6 receptor antibody after 3 months of storage at 40° C. Furthermore, the antibody-containing aqueous formulation of the present disclosure can retain at least 90% of monomer form of the anti-interleukin-6 receptor antibody after 3 months of storage at 40° C. The present disclosure will be further illustrated below with reference to specific examples, and within each of the examples, several formulation candidates with different compositions or pH values are provided. The following examples and materials described hereafter are for exemplary purposes only.

1. Material and Methods

In following formulation candidates provided by the present disclosure, Tocilizumab IgG is expressed in CHO-DG44 cells. CHO-DG44 cells are cultured in a 2,000-liter bioreactor, and fed-batch process was conducted. Tocilizumab IgG generated by the above process is purified by a standard series of chromatography steps known in the art, including rPA affinity chromatography, ion-exchange chromatography, and mix-mode chromatography. Tangential Flow Filtration is further performed to concentrate the above purified IgG proteins using ultra-filtration membrane, and a diafiltration is conducted to exchange selected buffer.

To assess buffer system affecting the stability and aggregate formation of Tocilizumab IgG, 20 mg/ml Tocilizumab IgG is formulated in various buffers (e.g., acetate buffer or histidine buffer) with addition of excipients. The commercially available Acterma® is used as a control group in the present disclosure. Acterma® comprises 20 mg/ml of Tocilizumab IgG, 15 mM of sodium phosphate buffer at pH 6.5, 5% of sucrose, and 0.05% of polysorbate 80.

The excipients are the protein stabilizer and the surfactant. The protein stabilizer may be sucrose or trehalose. The surfactant is not limited to polysorbate 80, polysorbate 20, or poloxamer.

Thermal stress, mechanical stress, oxidation stress, photo stress, and freeze-thaw stress are performed to evaluate the stability of Tocilizumab IgG in the formulation candidates. The conditions of these stress tests are listed in Table 1.

TABLE 1

The conditions of the thermal, mechanical, oxidative, photo and freeze-thaw stress tests.

| Stress Tests | Condition | Time Point(s) |
| --- | --- | --- |
| Thermal stress | 4° C. or 40° C. | 0, 8 weeks, 3 months or 6 months |
| Mechanical stress | Agitation with mini vortexer | 4 hr constant agitation |
| Oxidation stress | Tertiary Butyl Peroxide added at 1% w/v | 24 hrs |
| Photo stress | UV-light exposure (broad spectrum) | 24 hrs |
| Freeze-thaw stress | −70° C. to Room Temperature | 5 consecutive cycles |

1.1. IL-6R Binding Assay (Potency)

After purification or stress treatment, the samples containing Tocilizumab IgG are filled into the 96-well plate, of which the surface is coated with IL-6 receptors. After incubating for 24 hours, the binding reaction is terminated by adding acid solution, and binding efficiency is further analyzed.

1.2. Size Exclusion Chromatography-High Performance Liquid Chromatography (SEC-HPLC)

SEC-HPLC is used to monitor protein aggregation and fragmentation of the formulation candidates of the present disclosure, and determine the purity of Tocilizumab IgG of the formulation candidates of the present disclosure. About 200 μg of Tocilizumab IgG of each sample after stress treatment is injected for SEC-HPLC analysis.

Figure 2:
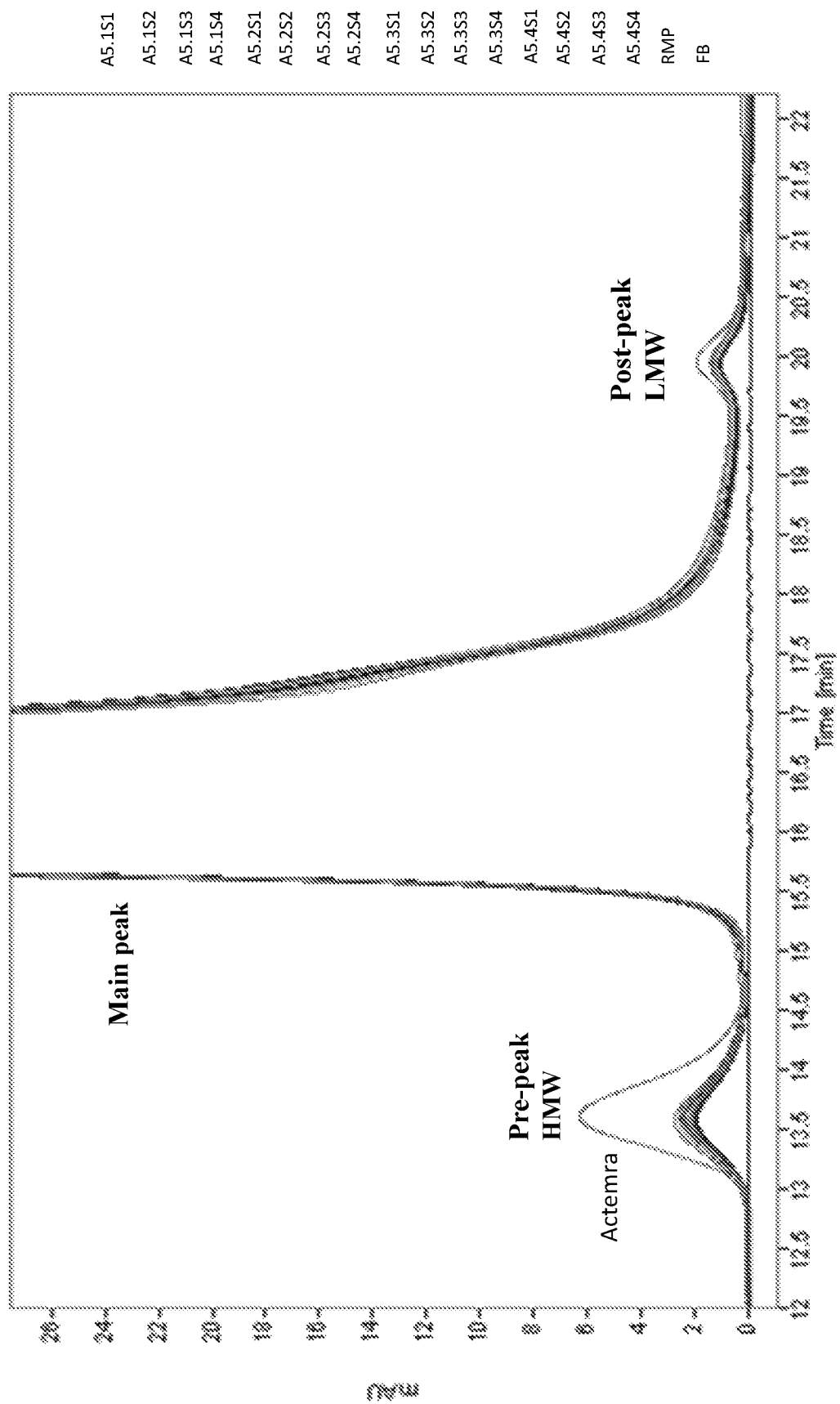
FIG. 2 is a SEC-HPLC profile of Tocilizumab IgG after being subjected to storage at 4° C. for 6 months, according to an exemplary embodiment of the present disclosure.
Figure 3:
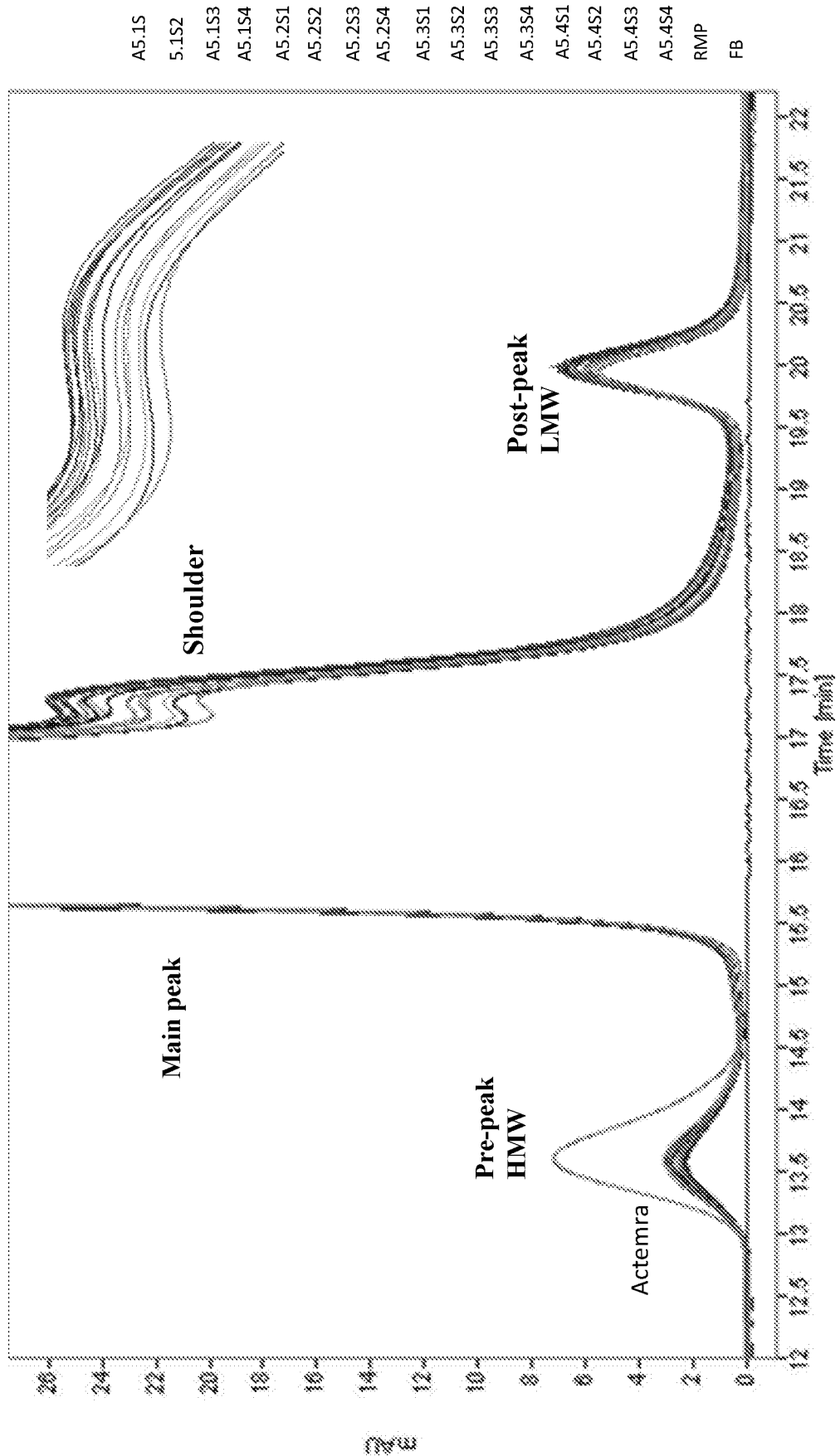
FIG. 3 is a SEC-HPLC profile of Tocilizumab IgG after being subjected to storage at 25° C. for 6 months, according to an exemplary embodiment of the present disclosure.

FIGS. 1-3 are SEC-HPLC profiles, in accordance with an embodiment of the present disclosure. In FIGS. 1-3, main peaks represent monomers of the Tocilizumab IgG; pre-peaks represent high molecular weight (HMW) aggregate formation of Tocilizumab IgG. Aggregate formation of Tocilizumab IgG increases risks for inducing immune response after being introduced into the human body. In FIGS. 1-3, post-peaks represent degraded low molecular weight (LMW) fragments of Tocilizumab IgG. The higher the main peaks represents higher purity and stability of the formulation.

1.3. FlowCam Analysis

The FlowCam analysis is used to monitor the sub-visible particles formed in the formulation comprising Tocilizumab IgG. According to US Parmacopeia Chapter <787> (USP<787>), the count of sub-visible particles of the therapeutic protein injection should be analyzed, and particles fell into the size range of >10 μm and >25 μm would be defined as sub-visible particles. Based on USP<787>, the count of particles with the size larger than 10 μm must be less than 6,000 particles/container, and the count of particles with the size larger than 25 μm must be less than 600 particles/container if the container volume is smaller than 100 mL. Larger sub-visible particles represent higher risk of immunogenicity. The FlowCam analysis is performed with the parameters detailed in Table 3.

TABLE 3

The conditions for FlowCam analysis

| | |
|---|---|
| Particle Segmentation | Dark Threshold 15.00; Light Threshold 15.00 |
| Distance to Nearest Neighbor | 0 microns |
| Close Holes | 5 iterations |
| Basic Size Filter | equivalent spherical diameter (ESD): Min 1.00, Max 10000.00 microns |
| Advanced Filter | None |
| Auto-Image Frame Rate | 39 frames per second |
| Flash Duration | 300.00 microseconds |
| Camera Gain | 0 |

2. Example 1: Effect of the Buffer System and Tonicifier on the Stability of Tocilizumab IgG To assess the impact of buffer system and tonicifier on the protein stability of Tocilizumab IgG, 20 mg/ml Tocilizumab IgG is formulated in various buffers (20 mM acetate, pH 4.5 or pH 5; 20 mM histidine, pH 6) with the addition of excipients containing 7% sucrose and 0.003% polysorbate 80. The buffers further include a tonicifier selected from 110 mM NaCl or 4% sorbitol. These prepared formulation candidates listed in Table 2 are subjected to thermal stress, mechanical stress, oxidative stress, photo stress and freeze-thaw stress tests to evaluate the stability of Tocilizumab IgG. The commercially available Actemra®, which comprises 20 mg/ml of Tocilizumab IgG, 15 mM of sodium phosphate buffer at pH 6.5, 5% of sucrose, and 0.05% of polysorbate 80, is taken as the Reference Medicinal Product (RMP).

TABLE 4

The composition of formulation candidates of Example 1 comprising Tocilizumab IgG.

| Formulation | Sample Description | Buffer | Target pH | Tonicity modifier | Stabilizer(s) | Polysorbate 80 (w/v %) |
|---|---|---|---|---|---|---|
| 1 | A4.5N | 20 mM Na Acetate | 4.5 | 110 mM NaCl | 7% Sucrose | 0.03 |
| 2 | A4.5S | 20 mM Na Acetate | 4.5 | 4% Sorbitol | 7% Sucrose | 0.03 |
| 3 | A5.0N | 20 mM Na Acetate | 5 | 110 mM NaCl | 7% Sucrose | 0.03 |
| 4 | A5.0S | 20 mM Na Acetate | 5 | 4% Sorbitol | 7% Sucrose | 0.03 |
| 5 | H6N | 20 mM Histidine | 6 | 110 mM NaCl | 7% Sucrose | 0.03 |
| 6 | H6S | 20 mM Histidine | 6 | 4% Sorbitol | 7% Sucrose | 0.03 |
| 7 | Actemra® DP | 15 mM Na Phosphate | 6.5 | | 5% Sucrose | 0.05% PS 80 |

2.1. Thermal Stress Test

The prepared formulation candidates are subjected to a storage time of 8 weeks (or 2 months) at −70° C., 4° C. or 40° C., and followed by further analysis. The following analyses after storage are pH value assay, amniotic fluid optical density at 650 nm ($OD_{650}$), protein concentration assay, binding ability assay, SEC-HPLC analysis, and Flow-Cam analysis.

2.1.1. pH, $OD_{650}$ and Protein Concentration Assay After Thermal Stress Test

The formulation candidates are analyzed for the pH value, protein concentration and amniotic fluid optical density at 650 nm ($OD_{650}$) following the 8 weeks of storage at the either 4° C. or 40° C. As shown in Table 5, the pH value, $OD_{650}$ value and protein concentration of each formulation candidate of the present disclosure has no significant change after being treated with thermal stress.

TABLE 5 pH, $OD_{650}$ and protein concentration of the formulation candidates of Example 1

| | pH value | | | $OD_{650}$ Temperature | | | Concentration (mg/mL) | | |
|---|---|---|---|---|---|---|---|---|---|
| | $T_0$ | 8 weeks | | $T_0$ | 8 weeks | | $T_0$ | 8 weeks | |
| | (control) | 4° C. | 40° C. | (control) | 4° C. | 40° C. | (control) | 4° C. | 40° C. |
| A4.5N | 4.52 | 4.46 | 4.60 | 0.006 | 0.004 | 0.005 | 20.57 | 20.77 | 20.77 |
| A4.5S | 4.61 | 4.47 | 4.66 | 0.002 | 0.001 | 0.012 | 20.62 | 20.89 | 20.82 |
| A5.0N | 4.96 | 4.92 | 4.99 | 0.002 | 0.003 | 0.003 | 20.64 | 19.91 | 20.72 |
| A5.0S | 5.02 | 4.94 | 5.05 | 0.000 | −0.010 | −0.009 | 20.36 | 20.41 | 20.72 |
| H6N | 6.16 | 6.03 | 6.07 | 0.000 | 0.009 | 0.001 | 21.67 | 21.88 | 19.53 |
| H6S | 6.12 | 6.10 | 6.08 | 0.003 | 0.002 | 0.002 | 19.21 | 19.39 | 19.53 |
| Actemra ® | 6.52 | 6.50 | 6.51 | 0.000 | 0.001 | 0.002 | 19.38 | 19.48 | 19.68 |

2.1.2. Potency of Tocilizumab IgG after Thermal Stress Test

The relative binding capacity of Tocilizumab IgG formulated in the formulation candidates of the present disclosure after being treated with different temperatures of thermal stress was measured by using enzyme-linked immunosorbent assay (ELISA).

As shown in Table 6, the binding activity of Tocilizumab IgG formulated in different buffer (including Actemra®) has no significant difference after being subjected to 8 weeks of storage at −70° C. or 4° C. compared with samples before being subjected to storage, but it slightly decreased after the storage at 40° C.

Further, Tocilizumab IgG formulated in A4.5N, A4.5S, A5.0N, A5.0S, H6N and H6S shows higher binding activity value than that formulated in the RMP, Actemra®, after being treated with thermal stress at 40° C., indicating that Tocilizumab IgG formulated in the above described formulation presented better thermostability than that formulated in Actermra®.

TABLE 6

Potency of Tocilizumab IgG in the formulation candidates of Example 1 after thermal stress

| | Potency % Temperature | | | | |
|---|---|---|---|---|---|
| Item | $T_0$ | −70° C. | 4° C. | 25° C. | 40° C. |
| A4.5N | 102.5 | 116.3 | 109.3 | 112.6 | 98.8 |
| A4.5S | 119.8 | 105 | 111.5 | 114.9 | 100.1 |
| A5.0N | 122.6 | 103.4 | 113.9 | 105.7 | 98 |
| A5.0S | 117.6 | 96.6 | 104.5 | 108.7 | 102.3 |
| H6N | 102.3 | 105.8 | 98.7 | 96 | 98 |
| H6S | 95.2 | 110.9 | 104.7 | 108.8 | 95.8 |
| Actemra ® | 115.7 | 114.4 | 123 | 119 | 94.2 |

2.1.3. SEC-HPLC Analysis after Thermal Stress Test

Tables 7 to 9 demonstrate the percentages of Tocilizumab IgG monomers (main peak %), aggregates (pre-peak %), and fragments (post-peak %) determined by the SEC-HPLC before being subjected to storage (To) or after being subjected to 8 weeks of storage at either 4° C. or 40° C.

In addition, the results in Table 9 indicate that formulations of H6N (95.34%) and H6S (95.18%) show higher percentage of main peak than Actemra® (94.67%) after storage for 8 weeks at 40° C.

Tables 7 to 9 also show that formulations comprising sorbitol has both less HMW aggregates (HMW %) and less aggregation increase (increased HMW %) than those containing 110 mM sodium chloride after thermal stress treatment. Further, the A4.5N formulation shows high decrease in main peak % and high increase in HMW % and LMW % after storage at 40° C. Based on the data, it is found that the presence of sorbitol improved the stability of Tocilizumab IgG, especially in low pH environment. However, a new generated pre-peak 3 (HMW aggregates) is detected in A4.5N and A4.5S formulations after a storage condition of 40° C. for 8 weeks.

In general, comparing to Actemra® (RMP), Tocilizumab IgG has less aggregation and similar or higher monomer-form when formulated in acetate buffer at pH 5 or in histidine buffer at pH 6 containing 4% sorbitol. Even under the storage condition of 40° C. for 8 weeks, the formulation of acetate buffer at pH 5 or histidine buffer at pH 6 comprising 4% sorbitol retains >90% monomers and forms <1% aggregates. The result indicates that Tocilizumab IgG formulated in the buffer of acetate (pH 5) or histidine (pH 6) comprising 4% of sorbitol, 7% of sucrose and 0.003% of polysorbate 80 has better thermostability than Tocilizumab IgG formulated in Actemra®.

TABLE 7

SEC-HPLC peak summary of the formulation candidates of Example 1

| | Pre-Peak 1% | Main Peak % | Post peak % | Sum area |
|---|---|---|---|---|
| $T_0$-A4.5N | 0.19 | 99.49 | 0.33 | 40048 |
| $T_0$-A4.5S | 0.14 | 99.46 | 0.41 | 41047 |
| $T_0$-A5.0N | 0.23 | 99.49 | 0.29 | 43137 |
| $T_0$-A5.0S | 0.15 | 99.43 | 0.42 | 41540 |
| $T_0$-H6N | 0.29 | 99.45 | 0.27 | 44002 |
| $T_0$-H6S | 0.25 | 99.45 | 0.31 | 38899 |
| $T_0$-RMP | 0.88 | 98.84 | 0.28 | 42739 |

TABLE 8

SEC-HPLC peak summary of the formulation candidates of Example 1, with the storage condition of 4° C. for 8 weeks

| | Pre-peak1 % | HMW % | Increased HMW % | Main peak % | Increased Main-peak % | LMW % | Increased LMW % | Post-peak 1 % | Post-peak1' | Post-peak | Sum area |
|---|---|---|---|---|---|---|---|---|---|---|---|
| 4C8W-A4.5N | 0.24 | 0.24 | 0.04 | 99.53 | −0.13 | 0.23 | 0.09 | 0.23 | 0.05 | 0.18 | 38682 |
| 4C8W-A4.5S | 0.15 | 0.15 | −0.01 | 99.69 | 0.00 | 0.16 | 0.02 | 0.16 | — | 0.16 | 38159 |
| 4C8W-A5.0N | 0.31 | 0.31 | 0.06 | 99.49 | −0.12 | 0.20 | 0.06 | 0.20 | 0.05 | 0.15 | 37565 |
| 4C8W-A5.0S | 0.18 | 0.18 | 0.00 | 99.62 | −0.05 | 0.20 | 0.06 | 0.20 | 0.05 | 0.15 | 37936 |
| 4C8W-H6.0N | 0.34 | 0.34 | 0.01 | 99.47 | −0.06 | 0.20 | 0.06 | 0.20 | 0.06 | 0.14 | 40959 |
| 4C8W-H6.0S | 0.28 | 0.28 | −0.02 | 99.51 | −0.05 | 0.21 | 0.07 | 0.21 | 0.06 | 0.15 | 35637 |
| 4C8W-ACTEMRA® | 0.72 | 0.72 | 0.02 | 99.16 | −0.03 | 0.12 | 0.01 | 0.12 | — | 0.12 | 36038 |

TABLE 9

SEC peak summary of the formulation candidates of Example 1, with the storage condition of 40° C. for 8 weeks

| | Pre-peak3 % | Pre-peak2 % | Pre-peak1 % | HMW % | Increased HMW % | Main peak % | Increased Main-peak % | LMW % | Increased LMW % | Shoulder peak % | Post-peak 1 % | Post-peak1 | Post-peak1' | Post-peak2 % | Sum area |
|---|---|---|---|---|---|---|---|---|---|---|---|---|---|---|---|
| 40C8W-A4.5N | 0.04 | — | 1.19 | 1.25 | 1.03 | 38.35 | −11.31 | 10.42 | 10.28 | 7.19 | 2.90 | 0.13 | 2.77 | 0.33 | 37940 |
| 40C8W-A4.5S | 0.03 | — | 0.29 | 0.26 | 0.10 | 93.22 | −6.47 | 6.53 | 6.39 | 4.82 | 1.71 | 0.09 | 1.62 | — | 37853 |
| 40C8W-A5.0N | — | — | 0.80 | 0.80 | 0.55 | 92.93 | −8.68 | 6.27 | 6.13 | 4.65 | 1.62 | 0.08 | 1.54 | — | 38164 |
| 40C8W-A5.0S | — | — | 0.31 | 0.31 | 0.33 | 94.66 | −5.01 | 5.03 | 4.39 | 3.80 | 1.23 | 0.06 | 1.17 | — | 37948 |
| 40C8W-H6.0N | — | — | 0.56 | 0.56 | 0.25 | 96.34 | −4.19 | 4.09 | 3.95 | 3.17 | 0.92 | 0.05 | 0.87 | — | 40112 |
| 40C8W-H6.0S | — | — | 0.40 | 0.40 | 0.10 | 95.18 | −4.38 | 4.43 | 4.27 | 3.46 | 0.95 | 0.05 | 0.90 | — | 35779 |
| 40C8W-ACTEMRA® | — | — | 1.03 | 1.03 | 0.33 | 94.67 | −4.52 | 4.29 | 4.18 | 3.35 | 0.94 | — | 0.94 | — | 35886 |

2.1.4. FlowCam Analysis after Thermal Stress Test

Tables 10 to 12 demonstrate the particle counts (the quantity of particles per milliliter, P/ML) of the formulation candidates determined by FlowCam analysis before being subjected to storage (To) or after being subjected to 8 weeks of storage at either 4° C. or 40° C. The numbers described in Tables represent the quantity of particles per milliliter in each formulation treated with thermal stress at selected temperature.

In Table 10 and Table 12, the formulations of A4.5S, A5.0S, H6N and H6S show similar particle count to Actemra®, before being subject to storage. After 8 weeks of storage at either 4° C., the formulations of A4.5N, A4.5S, A5.0N, A5.0S, and H6S are determined lower particle count in the size ranges of >10 μm and >25 μm than Actemra®. After 8 weeks of storage at 40° C., the formulations of A4.5N, A4.5S, A5.0N, A5.0S, H6N and H6S are determined lower particle count in the size ranges of >10 μm and >25 μm than Actemra®.

Based on Tables 10 to 12, the formulation candidates A4.5S, A5.0S, H6N and H6S show similar or even lower particle count in the size ranges of >10 μm and >25 μm to the Actemra® (RMP) before being subjected to storage (To) or after being subjected to 8 weeks of storage at either 4° C. or 40° C., indicating that these formulation might improve the thermostability of Tocilizumab IgG.

TABLE 10

FlowCam results of the formulation candidates of Example 1 after thermal stress test, before subjected to storage (T₀)

| P/ML | A4.5N | A4.5S | A5.0N | A5.0S | H6N | H6S | RMP |
|---|---|---|---|---|---|---|---|
| 1-2 μm | 6237 | 2379 | 3418 | 3235 | 6198 | 4489 | 7125 |
| 2-4 μm | 6394 | 2041 | 4516 | 2838 | 5206 | 4567 | 6078 |
| 4-6 μm | 862 | 393 | 763 | 549 | 828 | 722 | 1205 |
| 6-8 μm | 501 | 212 | 519 | 244 | 205 | 306 | 520 |
| 8-10 μm | 204 | 71 | 244 | 61 | 90 | 102 | 244 |
| 10-25 μm | 368 | 141 | 549 | 122 | 98 | 118 | 87 |
| >25 μm | 63 | 71 | 31 | 61 | 25 | 55 | 16 |

TABLE 11

FlowCam results of the formulation candidates of Example 1 after thermal stress, with a storage condition of 4° C. for 8 weeks

| 4C8W | A4.5N | A4.5S | A5.0N | A5.0S | H6N | H6S | RMP |
|---|---|---|---|---|---|---|---|
| 1-2 μm | 3198 | 1420 | 3816 | 2303 | 2227 | 2378 | 6309 |
| 2-4 μm | 2452 | 1095 | 3465 | 1356 | 2336 | 2154 | 6578 |
| 4-6 μm | 347 | 145 | 538 | 165 | 447 | 355 | 822 |
| 6-8 μm | 160 | 95 | 255 | 110 | 243 | 126 | 389 |
| 8-10 μm | 24 | 32 | 67 | 28 | 122 | 91 | 185 |
| 10-25 μm | 45 | 138 | 63 | 48 | 263 | 189 | 193 |
| >25 μm | 12 | 43 | 19 | 0 | 118 | 44 | 8 |

TABLE 12

FlowCam results of the formulation candidates of Example 1 after thermal stress, with a storage condition of 40° C. for 8 weeks

| 40C8W | A4.5N | A4.5S | A5.0N | A5.0S | H6N | H6S | RMP |
|---|---|---|---|---|---|---|---|
| 1-2 μm | 2973 | 1575 | 1471 | 2084 | 5770 | 5076 | 8758 |
| 2-4 μm | 3417 | 1051 | 1318 | 1435 | 5946 | 5032 | 9464 |
| 4-6 μm | 683 | 158 | 212 | 94 | 1215 | 834 | 1807 |
| 6-8 μm | 271 | 47 | 75 | 63 | 463 | 331 | 740 |
| 8-10 μm | 142 | 12 | 8 | 20 | 169 | 90 | 292 |
| 10-25 μm | 154 | 31 | 16 | 43 | 192 | 67 | 347 |
| >25 μm | 4 | 12 | 8 | 19 | 31 | 12 | 59 |

2.2. Freeze-Thaw Stress Test

The prepared formulation candidates are performed with freeze-thaw process. The process is accomplished by freezing the formulation at −70° C. and subsequently thawing the ice to room temperature. The cycle of freezing and thawing is repeated for 5 times consecutively. Then, the process followed by further analyses, including pH value assay, amniotic fluid optical density at 650 nm ($OD_{650}$), protein concentration assay, SEC-HPLC analysis, and FlowCam analysis.

2.2.1. pH, $OD_{650}$ and Protein Concentration Assay After Freeze/Thaw Stress Test According to data shown in Table 13, the pH value, $OD_{650}$ value and protein concentration of each of the formulation candidates has no significant change after freeze-thaw tests.

TABLE 13 pH, $OD_{650}$ and protein concentration assay results of the formulation candidates of Example 1, after freeze-thaw stress tests

| | pH value | | $OD_{650}$ | | Concentration (mg/mL) | |
|---|---|---|---|---|---|---|
| Temperature | control | Experiment | control | Experiment | control | Experiment |
| A4.5N | 4.51 | 4.56 | 0.001 | 0.003 | 20.76 | 20.675 |
| A4.5S | 4.61 | 4.64 | 0.007 | 0.000 | 20.76 | 20.692 |
| A5.0N | 5.00 | 4.95 | 0.003 | 0.003 | 20.74 | 20.708 |
| A5.0S | 5.04 | 5.01 | 0.000 | 0.000 | 20.76 | 20.639 |
| H6N | 6.09 | 6.10 | 0.003 | 0.001 | 21.83 | 21.621 |
| H6S | 6.11 | 6.13 | 0.000 | 0.000 | 19.46 | 19.234 |
| Actemra ® | 6.54 | 6.51 | 0.002 | 0.002 | 19.34 | 19.469 |

2.2.2. SEC-HPLC Analysis after Freeze-Thaw Stress Test

Table 14 shows SEC-HPLC measurements of the purity of Tocilizumab IgG formulated in the formulation candidates of the present disclosure. These measurements include the amount of monomer (main peak %) of remaining, the amount of aggregates (HMW %) and fragments (LMW %) formed in the samples and the increase in aggregates (increased HMW %) and fragments (increased LMW %).

The results described in Table 14 show that there were no obvious aggregates increase (increased HMW %) and fragments increase (increased LMW %) of Tocilizumab IgG in the tested formulation candidates after freeze-thaw tests.

TABLE 14

SEC-HPLC peak summary of the formulation candidates of Example 1, after freeze-thaw stress test

| | Pre-peak 1 % | HMW % | Increased HMW % | Main peak % | Increased Main-peak % | LMW % | Increased LMW % | Post-peak 1 % | Sum area |
|---|---|---|---|---|---|---|---|---|---|
| FT5-A4.5N | 0.2 | 0.20 | 0.00 | 99.70 | 0.04 | 0.10 | −0.04 | 0.10 | 38800340 |
| FT5-A4.5S | 0.15 | 0.15 | −0.01 | 99.75 | 0.06 | 0.09 | −0.05 | 0.09 | 37249128 |
| FT5-A5.0N | 0.24 | 0.24 | −0.01 | 99.66 | 0.05 | 0.09 | −0.05 | 0.09 | 38095255 |

TABLE 14-continued

SEC-HPLC peak summary of the formulation candidates of Example 1, after freeze-thaw stress test

| | Pre-peak 1 % | HMW % | Increased HMW % | Main peak % | Increased Main-peak % | LMW % | Increased LMW % | Post-peak 1 % | Sum area |
|---|---|---|---|---|---|---|---|---|---|
| FT5-A5.0S | 0.17 | 0.17 | −0.01 | 99.73 | 0.06 | 0.09 | −0.05 | 0.09 | 37348239 |
| FT5-H6.0N | 0.33 | 0.33 | 0.00 | 99.58 | 0.05 | 0.09 | −0.05 | 0.09 | 39220858 |
| FT5-H6.0S | 0.28 | 0.28 | −0.02 | 99.63 | 0.07 | 0.10 | −0.04 | 0.10 | 34769108 |
| FT5-ACTEMRA ® | 0.66 | 0.66 | −0.04 | 99.26 | 0.07 | 0.08 | −0.03 | 0.08 | 35072563 |

2.2.3. FlowCam Analysis after Freeze-Thaw Stress Test

The formulation candidates of the present disclosure treated with freeze-thaw cycles is further evaluated by using FlowCam analysis, to acquire particle count data. The particle count of the formulation candidates before being subjected to freeze-thaw processing (Control) is shown in Table 10. Tables 15 provides the particle count of the formulation candidates after being subjected to freeze/thaw cycles, and the formulations of A4.5N, A4.5S, A5.0N, A5.0S, and H6N are determined lower particle count in the size ranges of >10 μm and >25 μm than Actemra® (RMP).

Based on the data presented in Tables 10 and 15, it is found that the formulations candidates A5.0S and H6N show similar or even lower particle count in the size ranges of >10 μm and >25 μm to Actemra® (RMP) before or after being subjected to freeze-thaw cycles, indicating that these formulation candidates might prevent sub-visible particle formation of Tocilizumab IgG.

TABLE 15

FlowCam results of the formulation candidates of Example 1, after freeze-thaw tests

| P/ML | A4.5N | A4.5S | A5.0N | A5.0S | H6N | H6S | RMP |
|---|---|---|---|---|---|---|---|
| 1-2 μm | 4177 | 1725 | 1901 | 3791 | 1356 | 4819 | 15478 |
| 2-4 μm | 4993 | 2000 | 2051 | 5375 | 1790 | 5013 | 15425 |
| 4-6 μm | 1205 | 617 | 413 | 1674 | 315 | 765 | 2187 |
| 6-8 μm | 644 | 327 | 248 | 601 | 127 | 183 | 1026 |
| 8-10 μm | 412 | 141 | 98 | 128 | 135 | 91 | 389 |
| 10-25 μm | 269 | 268 | 368 | 158 | 427 | 365 | 704 |
| >25 μm | 0 | 30 | 0 | 0 | 0 | 206 | 0 |

2.3. Mechanical Stress Test: Agitation

Agitation is a form of mechanical stress, and can lead to the aggregation of the protein molecules. The formulation candidates are performed with agitation and followed by further analysis, including pH value assay, amniotic fluid optical density at 650 nm ($OD_{650}$), protein concentration assay, SEC analysis, and FlowCam analysis.

2.3.1. pH, $OD_{650}$ and Protein Concentration Assay after Mechanical Stress Test As shown in Table 16, the pH value, $OD_{650}$ value and protein concentration of each of the formulation candidates has no significant changes after the treatment of agitation.

TABLE 16 pH, $OD_{650}$ and protein concentration assay results of the formulation candidates of Example 1, after mechanical stress test (agitation)

| | pH value | | $OD_{650}$ | | Concentration (mg/mL) | |
|---|---|---|---|---|---|---|
| Temperature | control | Experiment | control | Experiment | control | Experiment |
| A4.5N | 4.51 | 4.5 | 0.001 | 0.002 | 20.76 | 20.63 |
| A4.5S | 4.61 | 4.61 | 0.007 | 0.009 | 20.76 | 20.71 |
| A5.0N | 5.00 | 4.98 | 0.003 | 0.004 | 20.74 | 20.71 |
| A5.0S | 5.04 | 5.03 | 0.000 | 0.000 | 20.76 | 20.55 |
| H6N | 6.09 | 6.06 | 0.003 | 0.001 | 21.83 | 21.65 |
| H6S | 6.11 | 6.10 | 0.000 | 0.000 | 19.46 | 19.19 |
| Actemra ® | 6.54 | 6.51 | 0.002 | 0.002 | 19.34 | 19.43 |

2.3.2. SEC Analysis after Mechanical Stress Test

Table 17 demonstrates the SEC-HPLC analyses results of the formulation candidates, after being subjected to agitation. The results of SEC-HPLC analyses show that there was no significant change in the amount of monomer (main peak %), aggregates (HMW %) and fragments (LMW %), indicating that there were no aggregate increase (increased HMW %) and fragment increase (increased LMW %) of Tocilizumab Ig after agitation stress.

TABLE 17

SEC-HPLC analyses results of the formulation candidates of Example 1, after mechanical stress test (agitation)

| | Pre-peak1 % | HMW % | Increased HMW % | Main peak % | Increased Main-peak % | LMW % | Increased LMW % | Post-peak % | Sum area |
|---|---|---|---|---|---|---|---|---|---|
| AGIT-A4.5N | 0.22 | 0.22 | 0.01 | 99.65 | −0.04 | 0.13 | 0.03 | 0.13 | 37655343 |
| AGIT-A4.5S | 0.14 | 0.14 | 0.00 | 99.73 | −0.02 | 0.13 | 0.02 | 0.13 | 36906315 |
| AGIT-A5.0N | 0.27 | 0.27 | 0.02 | 99.61 | −0.04 | 0.11 | 0.02 | 0.11 | 37506113 |
| AGIT-A5.0S | 0.15 | 0.15 | −0.01 | 99.68 | −0.06 | 0.16 | 0.06 | 0.16 | 38434929 |
| AGIT-H6.0N | 0.30 | 0.30 | 0.01 | 99.59 | −0.03 | 0.11 | 0.02 | 0.11 | 40258821 |
| AGIT-H6.0S | 0.26 | 0.26 | 0.01 | 99.62 | −0.03 | 0.13 | 0.02 | 0.13 | 35762186 |
| AGIT-Actemra® | 0.65 | 0.65 | 0.00 | 99.27 | −0.01 | 0.08 | 0.01 | 0.08 | 36717662 |

2.3.3. FlowCam Analysis After Mechanical Stress Test (Agitation)

Tables 18 and 19 demonstrate the particle counts of the formulation candidates by using FlowCam analysis before or after being subjected to agitation. The formulation candidates that are not subjected to agitation are labeled as non-agitation group in Table 18. Tables 18 and 19 show that the formulations candidates A4.5N, A4.5S, A5.0N, A5.0S and H6S in groups with agitation and without agitation presented similar or even lower number of particles per milliliter in the size ranges of >10 μm and >25 μm, when comparing with Actemra® (RMP). Further, there was no increase in the particle count in the size ranges of interest (>10 μm and >25 μm) in the FlowCam results of the formulation candidates A4.5N, A5.0S and H6S, when comparing to the non-agitation group.

TABLE 18

FlowCam results of the formulation candidates of Example 1 without agitation

| control | A4.5N | A4.5S | A5.0N | A5.0S | H6N | H6S | RMP |
|---|---|---|---|---|---|---|---|
| 1-2 μm | 3126 | 1972 | 2193 | 3745 | 5186 | 2074 | 4881 |
| 2-4 μm | 2704 | 3010 | 1960 | 4036 | 5193 | 4186 | 4836 |
| 4-6 μm | 435 | 621 | 270 | 646 | 1316 | 2486 | 931 |
| 6-8 μm | 198 | 322 | 113 | 277 | 1158 | 1221 | 387 |
| 8-10 μm | 106 | 31 | 45 | 66 | 906 | 374 | 156 |
| 10-25 μm | 119 | 31 | 38 | 158 | 1025 | 180 | 134 |
| >25 μm | 0 | 0 | 0 | 0 | 16 | 0 | 0 |

TABLE 19

FlowCam results of the formulation candidates of Example 1 with agitation

| Agitation | A4.5N | A4.5S | A5.0N | A5.0S | H6N | H6S | RMP |
|---|---|---|---|---|---|---|---|
| 1-2 μm | 5114 | 6155 | 15903 | 4652 | 5733 | 5289 | 10581 |
| 2-4 μm | 2978 | 3859 | 14683 | 2974 | 8679 | 5170 | 10417 |

TABLE 19-continued

FlowCam results of the formulation candidates of Example 1 with agitation

| Agitation | A4.5N | A4.5S | A5.0N | A5.0S | H6N | H6S | RMP |
|---|---|---|---|---|---|---|---|
| 4-6 μm | 238 | 486 | 2492 | 360 | 951 | 767 | 1841 |
| 6-8 μm | 52 | 172 | 723 | 142 | 225 | 253 | 791 |
| 8-10 μm | 15 | 82 | 211 | 105 | 106 | 82 | 274 |
| 10-25 μm | 22 | 45 | 151 | 90 | 145 | 164 | 125 |
| >25 μm | 0 | 0 | 0 | 0 | 0 | 0 | 8 |

2.4. Photo Stress Test

The formulation candidates are exposed to UV light for 5 hours with the power of 1.6 watts/hour and followed by further analyses, and these analyses includes pH value assay, amniotic fluid optical density at 650 nm ($OD_{650}$), protein concentration assay, and SEC-HPLC analysis.

2.4.1: pH, $OD_{650}$ and Protein Concentration Assay after Photo Stress Test According Table 20, the pH value, $OD_{650}$ value and protein concentration of each of the formulation candidates has no significant change after photo stress test.

TABLE 20 pH, OD$_{650}$ and protein concentration of the formulation candidates of Example 1, after photo stress test

| Temperature | pH value | | OD$_{650}$ | | Concentration (mg/mL) | |
|---|---|---|---|---|---|---|
| | control | Experiment | control | Experiment | control | Experiment |
| A4.5N | 4.50 | 4.52 | 0.001 | 0.000 | 20.76 | 20.63 |
| A4.5S | 4.61 | 4.60 | 0.000 | 0.001 | 20.76 | 20.71 |
| A5.0N | 4.98 | 5.00 | 0.000 | 0.000 | 20.74 | 20.71 |
| A5.0S | 5.03 | 5.03 | 0.004 | 0.003 | 20.76 | 20.55 |
| H6N | 6.09 | 6.08 | 0.003 | 0.004 | 21.83 | 21.65 |
| H6S | 6.14 | 6.13 | 0.001 | 0.003 | 19.46 | 19.19 |
| Actemra ® | 6.52 | 6.53 | 0.005 | 0.007 | 19.34 | 19.43 |

2.4.2. SEC Analysis after Photo Stress Test

Table 21 demonstrates SEC-HPLC peak summary of formulation candidates after being subjected to the photo stress test. The results described in Table 21 indicate that there was no significant change in the amount of fragments (i.e., no significant increase of fragments (increased LMW %)) of Tocilizumab IgG in each formulations after UV light exposure, and were also no significant change in the amount of protein monomers (Main peak %) and aggregates (HMW %) in the formulations, including A4.5N, A4.5S, A5.0N, A5.0S, H6N and H6S. The formulations of RMP (Actemra®, pH6.5) showed slight increase (about 0.5%) in aggregates level (HMW %) and slight decrease in monomers level (Main peak %) after UV light exposure.

TABLE 21

SEC-HPLC peak summary of the formulation candidates of Example 1, after photo stress test

| | Pre-peak 1 % | HMW % | Increased HMW % | Main peak % | Increased Main-peak % | LMW % | Increased LMW % | Post-peak % | Sum area |
|---|---|---|---|---|---|---|---|---|---|
| PHOTO-A4.5N | 0.24 | 0.24 | 0.02 | 99.63 | −0.02 | 0.13 | 0.00 | 0.13 | 37017495 |
| PHOTO-A4.5S | 0.15 | 0.15 | 0.00 | 99.70 | −0.02 | 0.15 | 0.02 | 0.15 | 36570334 |
| PHOTO-A5.0N | 0.31 | 0.31 | 0.05 | 99.57 | −0.05 | 0.12 | 0.00 | 0.12 | 38692464 |
| PHOTO-A5.0S | 0.17 | 0.17 | 0.01 | 99.69 | −0.02 | 0.14 | 0.01 | 0.14 | 36401540 |
| PHOTO-H6.0N | 0.35 | 0.35 | 0.04 | 99.52 | −0.05 | 0.13 | 0.01 | 0.13 | 38673652 |
| PHOTO-H6.0S | 0.29 | 0.29 | 0.03 | 99.58 | −0.02 | 0.13 | 0.00 | 0.13 | 33919777 |
| PHOTO-ACTEMRA ® | 1.20 | 1.20 | 0.52 | 98.71 | −0.53 | 0.09 | 0.01 | 0.09 | 34732505 |

2.5. Oxidation Stress Test

The formulation candidates of the present disclosure are exposed to 1% tert-butyl hydroperoxide (tBHP, the oxidant) for 24 hours and followed by further analyses. These analyses include pH value assay, amniotic fluid optical density at 650 nm (OD650), protein concentration assay, and SEC-HPLC analysis. Another group of the formulation candidates are not exposed to tBHP, and are designated as non-oxidation group.

2.5.1. pH, OD650 and Protein Concentration Assay after Oxidation Stress Test According to Table 22, there are no significant differences among the pH value, OD$_{650}$ value and protein concentration of each of the formulation candidates after exposure to the oxidant, when comparing with non-oxidation group.

TABLE 22 pH, $OD_{650}$ and protein concentrations of the formulation candidates of Example 1, after oxidation stress test

| Item | pH value | | $OD_{650}$ | | Concentration(mg/mL) | |
|---|---|---|---|---|---|---|
| | non-oxidation | Experiment | non-oxidation | Experiment | non-oxidation | Experiment |
| A4.5N | 4.51 | 4.52 | 0.003 | 0.004 | 20.39 | 19.56 |
| A4.5S | 4.61 | 4.61 | 0.002 | 0.003 | 20.36 | 19.68 |
| A5.0N | 5.09 | 5.01 | 0.004 | 0.004 | 19.68 | 19.75 |
| A5.0S | 5.05 | 5.05 | 0.002 | 0.002 | 20.10 | 19.53 |
| H6N | 6.05 | 6.11 | 0.003 | 0.002 | 20.85 | 20.74 |
| H6S | 6.09 | 6.17 | 0.005 | 0.001 | 18.65 | 18.31 |
| Actemra ® | 6.49 | 6.51 | 0.006 | 0.004 | 19.12 | 18.45 |

2.5.2. SEC Analysis after Oxidation Stress Test

Table 23 demonstrates the results of the SEC-HPLC analyses of the formulation candidates after exposure to the oxidant. The results described in Table 23 show that the tested formulations have no significant change in the amount of monomers (main peak %), aggregates (HMW %) and fragments (LMW %) (i.e., no significant increase or decrease of monomers, aggregates and fragments) of Tocilizumab IgG after exposure to the oxidant.

TABLE 23

SEC-HPLC peak summary of the formulation candidates of Example 1, after oxidation stress test

| | Pre-peak 1 % | HMW % | Increased HMW % | Main peak % | Increased Main-peak % | LMW % | Increased LMW % | Post-peak % | Sum area |
|---|---|---|---|---|---|---|---|---|---|
| OXI-A4.5N | 0.26 | 0.26 | 0.05 | 99.61 | −0.05 | 0.13 | 0.00 | 0.13 | 36856078 |
| OXI-A4.5S | 0.14 | 0.14 | 0.00 | 99.74 | 0.00 | 0.11 | −0.01 | 0.11 | 38535448 |
| OXI-A5.0N | 0.28 | 0.28 | 0.02 | 99.61 | −0.01 | 0.11 | 0.00 | 0.11 | 37557108 |
| OXI-A5.0S | 0.17 | 0.17 | 0.01 | 99.73 | 0.00 | 0.11 | 0.00 | 0.11 | 37303390 |
| OXI-H6.0N | 0.31 | 0.31 | −0.02 | 99.59 | 0.02 | 0.11 | 0.00 | 0.11 | 39217816 |
| OXI-H6.0S | 0.25 | 0.25 | −0.01 | 99.64 | 0.00 | 0.11 | 0.00 | 0.11 | 36039515 |
| OXI-ACTEMRA ® | 0.65 | 0.65 | −0.01 | 99.27 | 0.02 | 0.08 | −0.01 | 0.08 | 34532137 |

Based on the data obtained from various stress tests, Tocilizumab IgG formulated in acetate (pH 5.0) or histidine (pH 6.0) buffer has lower aggregate formation and sub-visible particles than those formulated in Actemra® (phosphate buffer at pH 6.5), after being subjected to a long-term storage at 40° C., a freeze-thaw processing, agitation stress, photo stress test, and oxidation stress test. Furthermore, after being subjected to a long-term storage condition of 40° C. and a freeze-thaw processing, the formulation candidates comprising 4% sorbitol have higher remaining Tocilizumab IgG monomers and less aggregate formation, than the formulations comprising 110 mM of sodium chloride.

As evidenced by the above data presented in Example 1, acetate or histidine buffer at pH5.0 to pH6.0 can be appropriate buffers to formulate Tocilizumab IgG. These buffers improve the stability of the antibody, and the addition of sorbitol might reduce the protein aggregation.

3. Example 2: Effect of pH and Sorbitol Concentration on the Stability of Tocilizumab IgG In Example 2 of the present disclosure, acetate is chosen as the buffer solution and further elucidate the effect of pH levels and sorbitol concentrations on the stability of Tocilizumab IgG. Table 24 lists the formulation candidates of Example 2 (hereinafter "acetate samples"). The formulation candidates of Example 2 comprise 20 mg/ml of Tocilizumab IgG with varying pH (ranging from pH 5.1 to 5.4) and sorbitol concentration (ranging from 1% to 4%). Once formulated, these acetate samples are stored at 4° C. for 3 to 6 months, at 25° C. for 3 to 6 months, or at 40° C. for 3 months (thermal stress test), and are subject to further analyses.

TABLE 24

The compositions of the formulation candidates of Example 2

| Formulation # | Sample Description | Buffer | Target pH | Sorbitol (w/v %) | Stabilizer | Polysorbate 80 (w/v %) | Target protein conc. (mg/mL) |
|---|---|---|---|---|---|---|---|
| 1 | A5.1S1 | 20 mM Na Acetate | 5.1 | 1% Sorbitol | 7% Sucrose | 0.03 | 20 |
| 2 | A5.1S2 | 20 mM Na Acetate | 5.1 | 2% Sorbitol | 7% Sucrose | 0.03 | 20 |
| 3 | A5.1S3 | 20 mM Na Acetate | 5.1 | 3% Sorbitol | 7% Sucrose | 0.03 | 20 |
| 4 | A5.1S4 | 20 mM Na Acetate | 5.1 | 4% Sorbitol | 7% Sucrose | 0.03 | 20 |
| 5 | A5.2S1 | 20 mM Na Acetate | 5.2 | 1% Sorbitol | 7% Sucrose | 0.03 | 20 |
| 6 | A5.2S2 | 20 mM Na Acetate | 5.2 | 2% Sorbitol | 7% Sucrose | 0.03 | 20 |
| 7 | A5.2S3 | 20 mM Na Acetate | 5.2 | 3% Sorbitol | 7% Sucrose | 0.03 | 20 |
| 8 | A5.2S4 | 20 mM Na Acetate | 5.2 | 4% Sorbitol | 7% Sucrose | 0.03 | 20 |
| 9 | A5.3S1 | 20 mM Na Acetate | 5.3 | 1% Sorbitol | 7% Sucrose | 0.03 | 20 |
| 10 | A5.3S2 | 20 mM Na Acetate | 5.3 | 2% Sorbitol | 7% Sucrose | 0.03 | 20 |
| 11 | A5.3S3 | 20 mM Na Acetate | 5.3 | 3% Sorbitol | 7% Sucrose | 0.03 | 20 |
| 12 | A5.3S4 | 20 mM Na Acetate | 5.3 | 4% Sorbitol | 7% Sucrose | 0.03 | 20 |
| 13 | A5.4S1 | 20 mM Na Acetate | 5.4 | 1% Sorbitol | 7% Sucrose | 0.03 | 20 |
| 14 | A5.4S2 | 20 mM Na Acetate | 5.4 | 2% Sorbitol | 7% Sucrose | 0.03 | 20 |
| 15 | A5.4S3 | 20 mM Na Acetate | 5.4 | 3% Sorbitol | 7% Sucrose | 0.03 | 20 |
| 16 | A5.4S4 | 20 mM Na Acetate | 5.4 | 4% Sorbitol | 7% Sucrose | 0.03 | 20 |

3.1 pH, $OD_{650}$ and Protein Concentration assay after Thermal Stress Test

The acetate samples are analyzed for the pH value, protein concentration, and amniotic fluid optical density at 650 nm ($OD_{650}$) following the 3 to 6 months of storage at the 4° C., 25° C., or 40° C. The storage conditions with different temperatures are thermal stress tests for the acetate samples.

As shown in Tables 25, after a long-term storage at a lower temperature (4° C.), room temperature (25° C.) or elevated temperature (40° C.), the pH value, $OD_{650}$ value and protein concentration of each of the formulation candidates has no significant change.

TABLE 25 pH, OD$_{650}$ and protein concentrations assay of the formulation candidates of Example 2, after thermal stress test

| Item | pH value | | | | | | Concentration (mg/mL) | | | | | |
|---|---|---|---|---|---|---|---|---|---|---|---|---|
| | T$_0$ | 3 months | | | 6 months | | T$_0$ | 3 months | | | 6 months | |
| Temperature | (control) | 4° C. | 25° C. | 40° C. | 4° C. | 25° C. | (control) | 4° C. | 25° C. | 40° C. | 4° C. | 25° C. |
| A5.1S1 | 5.08 | 5.14 | 5.14 | 5.14 | 5.12 | 5.13 | 20.108 | 19.972 | 20.004 | 19.401 | 19.851 | 19.917 |
| A5.1S2 | 5.11 | 5.13 | 5.13 | 5.12 | 5.13 | 5.13 | 20.281 | 20.139 | 20.032 | 19.764 | 19.959 | 20.235 |
| A5.1S3 | 5.10 | 5.12 | 5.11 | 5.11 | 5.11 | 5.13 | 20.391 | 20.009 | 20.084 | 20.034 | 20.011 | 20.062 |
| A5.1S4 | 5.13 | 5.15 | 5.16 | 5.17 | 5.16 | 5.15 | 20.713 | 20.390 | 20.383 | 20.233 | 20.546 | 20.562 |
| A5.2S1 | 5.20 | 5.22 | 5.21 | 5.20 | 5.22 | 5.22 | 20.861 | 20.403 | 20.433 | 20.195 | 20.227 | 20.188 |
| A5.2S2 | 5.16 | 5.20 | 5.21 | 5.20 | 5.21 | 5.20 | 20.454 | 20.177 | 20.109 | 20.105 | 20.234 | 20.010 |
| A5.2S3 | 5.24 | 5.29 | 5.28 | 5.26 | 5.27 | 5.27 | 20.511 | 20.429 | 19.138 | 19.935 | 18.444 | 20.125 |
| A5.2S4 | 5.22 | 5.26 | 5.26 | 5.24 | 5.26 | 5.26 | 20.356 | 20.112 | 20.175 | 19.822 | 20.107 | 19.963 |
| A5.3S1 | 5.33 | 5.37 | 5.39 | 5.38 | 5.35 | 5.39 | 20.511 | 20.068 | 20.057 | 19.996 | 20.253 | 20.045 |
| A5.3S2 | 5.25 | 5.30 | 5.30 | 5.29 | 5.30 | 5.30 | 20.576 | 20.357 | 20.191 | 20.175 | 20.378 | 20.179 |
| A5.3S3 | 5.32 | 5.36 | 5.37 | 5.36 | 5.34 | 5.37 | 20.609 | 20.276 | 20.178 | 20.182 | 20.107 | 20.101 |
| A5.3S4 | 5.27 | 5.30 | 5.31 | 5.30 | 5.32 | 5.31 | 20.704 | 20.475 | 20.285 | 20.211 | 20.252 | 20.217 |
| A5.4S1 | 5.40 | 5.42 | 5.44 | 5.41 | 5.41 | 5.44 | 20.418 | 20.068 | 19.956 | 19.930 | 19.908 | 19.826 |
| A5.4S2 | 0.40 | 5.41 | 5.43 | 5.41 | 5.43 | 5.43 | 20.324 | 19.992 | 19.978 | 19.811 | 19.912 | 19.925 |
| A5.4S3 | 0.43 | 5.46 | 5.46 | 5.44 | 5.46 | 5.46 | 20.360 | 20.232 | 20.051 | 20.034 | 20.020 | 19.966 |
| A5.4S4 | 0.36 | 5.40 | 5.40 | 5.38 | 5.41 | 5.40 | 20.668 | 20.477 | 20.427 | 19.884 | 20.317 | 20.293 |
| Actemra ® | 6.46 | 6.49 | 6.51 | 5.49 | 5.48 | 6.31 | 19.765 | 19.591 | 19.573 | 19.241 | 19.544 | 19.295 |

3.2 SEC-HPLC Analysis after Thermal Stress Test

The acetate samples after thermal stress treatment are further analyzed using SEC-HPLC. FIGS. 1, 2, and 3 show SEC-HPLC profile of Tocilizumab IgG before being subjected to storage (To) or after being subjected to storage at 4° C. or 25° C. for 6 months. The area of pre-peak, main-peak and post-peak were integrated to calculate the proportion of aggregates, monomers and fragments of Tocilizumab IgG, and the result of calculation were presented in Tables 26 to 29.

Tables 26 to 29 demonstrate the percentage of Tocilizumab IgG monomers (main peak %), aggregates (HMW %), and fragments (LMW %) of the acetate samples by the SEC-HPLC analysis, before being subjected to storage (T$_0$) or after being subjected to storage at 4° C., 25° C., or 40° C. for 3 to 6 months.

As shown in Tables 26, 27-1, and 27-2, each of the acetate samples has similar percentage of Tocilizumab IgG monomers (main peak %), aggregates (HMW %), and fragments (LMW %). In Tables 26, 27-1, and 27-2, Actemra® has more aggregates (HMW %: 0.6~0.8%) and aggregate increase (Increased HMW %: 0.11~0.14%) than other samples (HMW %: 0.2~0.35%; Increased HMW %: 0.01~0.08%) either before being subjected to storage (To) or after being subjected to storage at 4° C. for 3 to 6 months.

After storing at 25° C. for 3 months, the acetate samples show similar results to the acetate samples before being subjected to storage (To) (see Table 28-1). However, as the storage time is prolonged to 6 months, the percentage of monomers (main peak %) slightly decreases, the percentage of fragments (LMW %) slightly increases, and the shoulder appears (FIG. 3.). Moreover, the fragments and shoulder formation of the acetate samples decrease along with the increase in pH level, and the fragments and shoulder formation of the acetate samples increase along with the increase in sorbitol concentration (see Table 27-2). The phenomena aforementioned could be observed more evidently when the acetate samples are subjected to storage at 40° C. for 3 months.

Table 29 also shows that Actemra® has more aggregates (HMW %: 1.59%) and higher aggregate increase (Increased HMW %: 0.93%) than other acetate samples (HMW %: 0.4-0.6%; Increased HMW %: 0.2-0.3%) after being subjected to 3 months of storage at 40° C. Further, the fragment formation of the acetate samples decreased with the increase of pH level, and the acetate samples with higher sorbitol concentration shows more monomer loss than the acetate samples with lower sorbitol concentration at the same pH condition, after being stored at 40° C. for 3 months.

TABLE 26

SEC-HPLC peak summary of the formulation candidates of Example 2, before being subjected to storage (T$_0$)

| Sample Number | HMW % | Main peak % | LMW % | Sum area |
|---|---|---|---|---|
| A5.1S1 | 0.23 | 99.75 | 0.02 | 34728150 |
| A5.1S2 | 0.23 | 99.75 | 0.02 | 37277772 |
| A5.1S3 | 0.20 | 99.77 | 0.02 | 35029061 |
| A5.1S4 | 0.23 | 99.75 | 0.02 | 38021887 |
| A5.2S1 | 0.22 | 99.75 | 0.02 | 35204088 |
| A5.2S2 | 0.25 | 99.73 | 0.03 | 35213791 |
| A5.2S3 | 0.25 | 99.73 | 0.02 | 35274716 |
| A5.2S4 | 0.21 | 99.77 | 0.02 | 34901083 |
| A5.3S1 | 0.25 | 99.73 | 0.02 | 35001255 |
| A5.3S2 | 0.25 | 99.72 | 0.02 | 36387499 |
| A5.3S3 | 0.25 | 99.72 | 0.03 | 36456144 |
| A5.3S4 | 0.25 | 99.72 | 0.02 | 35852816 |
| A5.4S1 | 0.26 | 99.71 | 0.02 | 35366994 |
| A5.4S2 | 0.27 | 99.71 | 0.02 | 37254869 |
| A5.4S3 | 0.26 | 99.71 | 0.02 | 35635718 |
| A5.4S4 | 0.26 | 99.71 | 0.02 | 37309692 |
| Actemra ® | 0.66 | 99.26 | 0.09 | 36579732 |

TABLE 27-1

SEC-HPLC peak summary of the formulation candidates of Example 2, with a storage condition of 4° C. for 3 months

| Sample Number | HMW % | Increased HMW % | Main peak % | Increased Main-peak % | LMW % | Increased LMW % | Sum area |
|---|---|---|---|---|---|---|---|
| A5.1S1 | 0.26 | 0.03 | 99.60 | −0.15 | 0.14 | 0.12 | 36036.3 |
| A5.1S2 | 0.25 | 0.02 | 99.61 | −0.14 | 0.14 | 0.12 | 36568.4 |
| A5.1S3 | 0.24 | 0.04 | 99.60 | −0.17 | 0.16 | 0.14 | 36245.9 |
| A5.1S4 | 0.25 | 0.02 | 99.57 | −0.18 | 0.18 | 0.16 | 37061.9 |
| A5.2S1 | 0.26 | 0.04 | 99.60 | −0.15 | 0.14 | 0.12 | 36841.7 |
| A5.2S2 | 0.26 | 0.01 | 99.60 | −0.13 | 0.14 | 0.11 | 37926.5 |
| A5.2S3 | 0.27 | 0.02 | 99.58 | −0.15 | 0.15 | 0.13 | 36856 |
| A5.2S4 | 0.26 | 0.05 | 99.56 | −0.21 | 0.18 | 0.16 | 36951.9 |
| A5.3S1 | 0.29 | 0.04 | 99.57 | −0.16 | 0.14 | 0.12 | 36267.7 |
| A5.3S2 | 0.28 | 0.03 | 99.58 | −0.14 | 0.14 | 0.12 | 36895.7 |
| A5.3S3 | 0.29 | 0.04 | 99.58 | −0.14 | 0.12 | 0.09 | 36833 |
| A5.3S4 | 0.29 | 0.04 | 99.62 | −0.10 | 0.09 | 0.07 | 36381.8 |
| A5.4S1 | 0.32 | 0.06 | 99.59 | −0.12 | 0.10 | 0.08 | 36228.2 |
| A5.4S2 | 0.30 | 0.03 | 99.60 | −0.11 | 0.10 | 0.08 | 36278.1 |
| A5.4S3 | 0.30 | 0.04 | 99.58 | −0.13 | 0.11 | 0.09 | 36630.1 |
| A5.4S4 | 0.29 | 0.03 | 99.58 | −0.13 | 0.13 | 0.11 | 37237.9 |
| Actemra ® | 0.80 | 0.14 | 99.06 | −0.20 | 0.14 | 0.05 | 36661.2 |

TABLE 27-2

SEC-HPLC peak summary of the formulation candidates of Example 2, with a storage condition of 4° C. for 6 months

| Sample Number | HMW % | Increase HMW % | Main peak % | Increased Main-peak % | LMW % | Increase LMW % | Sum area |
|---|---|---|---|---|---|---|---|
| A5.1S1 | 0.26 | 0.03 | 99.62 | −0.13 | 0.12 | 0.10 | 36700.1306 |
| A5.1S2 | 0.26 | 0.03 | 99.61 | −0.14 | 0.13 | 0.11 | 36873.4974 |
| A5.1S3 | 0.25 | 0.05 | 99.63 | −0.14 | 0.12 | 0.10 | 36997.9602 |
| A5.1S4 | 0.27 | 0.04 | 99.61 | −0.14 | 0.12 | 0.10 | 37065.4542 |
| A5.2S1 | 0.27 | 0.05 | 99.60 | −0.15 | 0.13 | 0.11 | 38330.5265 |
| A5.2S2 | 0.28 | 0.03 | 99.60 | −0.13 | 0.13 | 0.10 | 41433.2793 |
| A5.2S3 | 0.31 | 0.06 | 99.57 | −0.16 | 0.12 | 0.10 | 34535.3855 |
| A5.2S4 | 0.27 | 0.06 | 99.62 | −0.15 | 0.12 | 0.10 | 36914.0760 |
| A5.3S1 | 0.33 | 0.08 | 99.49 | −0.24 | 0.17 | 0.15 | 37886.8534 |
| A5.3S2 | 0.31 | 0.06 | 99.55 | −0.17 | 0.14 | 0.12 | 38126.3745 |
| A5.3S3 | 0.31 | 0.06 | 99.57 | −0.15 | 0.13 | 0.10 | 37415.7769 |
| A5.3S4 | 0.29 | 0.04 | 99.57 | −0.15 | 0.13 | 0.11 | 37675.9355 |
| A5.4S1 | 0.32 | 0.06 | 99.53 | −0.18 | 0.14 | 0.12 | 36918.7516 |
| A5.4S2 | 0.31 | 0.04 | 99.54 | −0.17 | 0.14 | 0.12 | 36891.8872 |
| A5.4S3 | 0.31 | 0.05 | 99.54 | −0.17 | 0.15 | 0.13 | 37506.6960 |
| A5.4S4 | 0.30 | 0.04 | 99.50 | −0.21 | 0.20 | 0.18 | 37805.3653 |
| Actemra ® | 0.77 | 0.11 | 98.99 | −0.27 | 0.24 | 0.15 | 36135.7490 |

TABLE 28-1

SEC-HPLC peak summary of the formulation candidates of Example 2, with a storage condition of 25° C. for 3 months

| Sample Number | HMW % | Increased HMW % | Main peak % | Increased Main-peak % | LMW % | Increased LMW % | Sum area |
|---|---|---|---|---|---|---|---|
| A5.1S1 | 0.28 | 0.05 | 99.38 | −0.37 | 0.35 | 0.33 | 35789.3 |
| A5.1S2 | 0.27 | 0.04 | 99.38 | −0.37 | 0.35 | 0.33 | 36407.1 |
| A5.1S3 | 0.25 | 0.05 | 99.37 | −0.4 | 0.38 | 0.36 | 36364.4 |
| A5.1S4 | 0.27 | 0.04 | 99.32 | −0.43 | 0.41 | 0.39 | 36821.6 |
| A5.2S1 | 0.29 | 0.07 | 99.36 | −0.39 | 0.35 | 0.33 | 36982.7 |
| A5.2S2 | 0.29 | 0.04 | 99.36 | −0.37 | 0.35 | 0.32 | 36348.3 |
| A5.2S3 | 0.32 | 0.07 | 99.34 | −0.39 | 0.33 | 0.31 | 36022.5 |
| A5.2S4 | 0.28 | 0.07 | 99.33 | −0.44 | 0.39 | 0.37 | 36027.7 |
| A5.3S1 | 0.33 | 0.08 | 99.35 | −0.38 | 0.32 | 0.3 | 36072.8 |
| A5.3S2 | 0.31 | 0.06 | 99.36 | −0.36 | 0.33 | 0.31 | 36950.7 |
| A5.3S3 | 0.32 | 0.07 | 99.34 | −0.38 | 0.34 | 0.31 | 36617.7 |
| A5.3S4 | 0.31 | 0.06 | 99.34 | −0.38 | 0.35 | 0.33 | 36504 |
| A5.4S1 | 0.35 | 0.09 | 99.34 | −0.37 | 0.31 | 0.29 | 36125.8 |

TABLE 28-1-continued

SEC-HPLC peak summary of the formulation candidates of Example 2, with a storage condition of 25° C. for 3 months

| Sample Number | HMW % | Increased HMW % | Main peak % | Increased Main-peak % | LMW % | Increased LMW % | Sum area |
|---|---|---|---|---|---|---|---|
| A5.4S2 | 0.34 | 0.07 | 99.36 | −0.35 | 0.31 | 0.29 | 36430.5 |
| A5.4S3 | 0.34 | 0.08 | 99.33 | −0.38 | 0.33 | 0.31 | 36532.8 |
| A5.4S4 | 0.32 | 0.06 | 98.32 | −0.39 | 0.36 | 0.34 | 36961.9 |
| Actemra ® | 0.83 | 0.17 | 98.82 | −0.44 | 0.35 | 0.26 | 35899.8 |

TABLE 28-2

SEC-HPLC peak summary of the formulation candidates of Example 2, with a storage condition of 25° C. for 6 months

| Sample Number | HMW % | Increased HMW % | Main peak % | Increased Main-peak % | Shoulder % | Increased Shoulder % | LMW % | Increased LMW % | Sum area |
|---|---|---|---|---|---|---|---|---|---|
| A5.1S1 | 0.30 | 0.07 | 97.06 | −2.69 | 2.07 | 2.07 | 0.57 | 0.55 | 39150.1953 |
| A5.1S2 | 0.30 | 0.07 | 97.04 | −2.71 | 2.09 | 2.09 | 0.58 | 0.56 | 39098.1052 |
| A5.1S3 | 0.28 | 0.08 | 97.04 | −2.73 | 2.11 | 2.11 | 0.57 | 0.55 | 37678.7645 |
| A5.1S4 | 0.30 | 0.07 | 96.96 | −2.79 | 2.16 | 2.16 | 0.57 | 0.55 | 37576.8264 |
| A5.2S1 | 0.32 | 0.10 | 97.14 | −2.61 | 2.00 | 2.00 | 0.54 | 0.52 | 37759.4751 |
| A5.2S2 | 0.31 | 0.06 | 97.12 | −2.61 | 2.02 | 2.02 | 0.55 | 0.52 | 37465.7636 |
| A5.2S3 | 0.32 | 0.07 | 97.12 | −2.61 | 2.02 | 2.02 | 0.55 | 0.53 | 37986.3794 |
| A5.2S4 | 0.31 | 0.10 | 97.01 | −2.76 | 2.13 | 2.13 | 0.55 | 0.53 | 36921.7585 |
| A5.3S1 | 0.36 | 0.11 | 97.27 | −2.46 | 1.87 | 1.87 | 0.50 | 0.48 | 37376.7372 |
| A5.3S2 | 0.35 | 0.10 | 97.23 | −2.49 | 1.91 | 1.91 | 0.52 | 0.50 | 41207.2882 |
| A5.3S3 | 0.36 | 0.11 | 97.25 | −2.47 | 1.87 | 1.87 | 0.51 | 0.48 | 37445.9972 |
| A5.3S4 | 0.35 | 0.10 | 97.02 | −2.70 | 2.08 | 2.08 | 0.54 | 0.52 | 37688.2849 |
| A5.4S1 | 0.39 | 0.13 | 97.36 | −2.35 | 1.78 | 1.78 | 0.48 | 0.46 | 37215.9016 |
| A5.4S2 | 0.38 | 0.11 | 97.34 | −2.37 | 1.80 | 1.80 | 0.49 | 0.47 | 36885.3817 |
| A5.4S3 | 0.38 | 0.12 | 97.36 | −2.35 | 1.78 | 1.78 | 0.48 | 0.46 | 37146.1753 |
| A5.4S4 | 0.36 | 0.10 | 97.33 | −2.38 | 1.82 | 1.82 | 0.49 | 0.47 | 37572.7428 |
| Actemra ® | 0.89 | 0.23 | 96.79 | −2.47 | 1.79 | 1.79 | 0.54 | 0.45 | 35998.7191 |

TABLE 29

SEC-HPLC peak summary of the formulation candidates of Example 2, with a storage condition of 40° C. for 3 months

| Sample Number | HMW % | Increased HMW % | Main peak % | Increased Main-peak % | Shoulder % | LMW % | Increased LMW % | Sum area |
|---|---|---|---|---|---|---|---|---|
| A5.1S1 | 0.52 | 0.29 | 93.1 | −6.65 | 4.7 | 1.69 | 1.67 | 35252.1818 |
| A5.1S2 | 0.45 | 0.22 | 93.15 | −6.6 | 4.73 | 1.67 | 1.65 | 36033.6966 |
| A5.1S3 | 0.41 | 0.21 | 93.02 | −6.75 | 4.96 | 1.61 | 1.59 | 35958.8232 |
| A5.1S4 | 0.58 | 0.35 | 92.55 | −7.2 | 5.25 | 1.62 | 1.6 | 36766.0109 |
| A5.2S1 | 0.47 | 0.25 | 93.49 | −6.26 | 4.47 | 1.57 | 1.55 | 36405.2105 |
| A5.2S2 | 0.46 | 0.21 | 93.47 | −6.26 | 4.49 | 1.58 | 1.55 | 36634.0103 |
| A5.2S3 | 0.46 | 0.21 | 93.47 | −6.26 | 4.6 | 1.47 | 1.45 | 36099.1330 |
| A5.2S4 | 0.43 | 0.22 | 93.1 | −6.67 | 4.95 | 1.52 | 1.5 | 35831.3562 |
| A5.3S1 | 0.52 | 0.27 | 93.91 | −5.82 | 4.15 | 1.43 | 1.41 | 36656.3546 |
| A5.3S2 | 0.5 | 0.25 | 93.72 | −6 | 4.29 | 1.49 | 1.47 | 36394.4932 |
| A5.3S3 | 0.54 | 0.29 | 93.1 | −6.62 | 4.83 | 1.54 | 1.51 | 36389.1406 |
| A5.3S4 | 0.51 | 0.26 | 92.77 | −6.95 | 5.13 | 1.59 | 1.57 | 36247.9774 |
| A5.4S1 | 0.6 | 0.34 | 93.71 | −6 | 4.22 | 1.46 | 1.44 | 35977.0024 |
| A5.4S2 | 0.51 | 0.24 | 94.31 | −5.4 | 3.87 | 1.31 | 1.29 | 35336.2693 |
| A5.4S3 | 0.52 | 0.26 | 93.84 | −5.87 | 4.33 | 1.32 | 1.3 | 36072.3756 |
| A5.4S4 | 0.52 | 0.26 | 93.68 | −6.03 | 4.47 | 1.33 | 1.31 | 35562.8917 |
| Actemra ® | 1.59 | 0.93 | 93.26 | −6 | 3.82 | 1.34 | 1.25 | 35040.7368 |

The above test data obtained from Example 2 is demonstrated that the acetate samples have less protein aggregates formation than Actemra®, after a long-term storage at 4° C., 25° C., or 40° C. The acetate samples with higher pH level has less shoulder and fragments formation, and the acetate samples containing higher sorbitol concentration has higher monomer loss and higher shoulder and fragments formation, after the long-term storage at 25° C. and 40° C.

As evidenced by the above results, the acetate buffer having higher pH level and lower sorbitol concentration improve the thermostability in the Tocilizumab IgG formulation. Therefore, the formulation candidates of the present disclosure having higher pH level and lower sorbitol concentration are better formulation than Actemra®.

In sum, according to various embodiments of the present disclosure, the antibody-containing aqueous formulations having pH values of 4.5 to 6.5 can stabilize and reduce aggregate formation of the anti-interleukin-6 receptor antibody in the antibody-containing aqueous formulation. The antibody-containing aqueous formulations provided by the present disclosure are thermostable, therefore can be stored at 4° C., 25° C., or 40° C. for at least 3 months.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. An antibody-containing aqueous formulation, comprising:
    a therapeutically effective amount of an anti-interleukin-6 receptor antibody;
    a protein stabilizer;
    a surfactant;
    a sorbitol tonicifier; and
    a buffer;
    wherein the anti-interleukin-6 receptor antibody is 5 mg/ml to 30 mg/ml of Tocilizumab IgG; the protein stabilizer is 4% (w/v) to 7% (w/v) of sucrose; the surfactant is 0.01% (w/v) to 0.05% (w/v) of polysorbate 80; the buffer is 10 mM to 30 mM of acetate buffer; and the antibody-containing aqueous formulation has a pH ranging between 5.0 and 6.0.

2. The antibody-containing aqueous formulation according to claim 1, wherein said sorbitol tonicifier is 1% (w/v) to 4% (w/v).

3. The antibody-containing aqueous formulation according to claim 1, wherein the antibody-containing aqueous formulation is administered to a subject by intravenous injection or infusion.

4. The antibody-containing aqueous formulation according to claim 1, wherein the antibody-containing aqueous formulation forms less than 5% of aggregates of the anti-interleukin-6 receptor antibody after 3 months of storage at 40° C.

5. The antibody-containing aqueous formulation according to claim 1, wherein at least 90% of the anti-interleukin-6 receptor antibody in the antibody-containing aqueous formulation is in monomer form after 3 months of storage at 40° C.

6. The antibody-containing aqueous formulation according to claim 1, wherein the antibody-containing aqueous formulation forms less than 5% of aggregates and at least 90% of the anti-interleukin-6 receptor antibody in the antibody-containing aqueous formulation is in monomer form after 3 months of storage at 40° C.

7. A method of suppressing aggregate formation of anti-interleukin-6 receptor antibody in an antibody-containing aqueous formulation, comprising steps of:
    formulating the anti-interleukin-6 receptor antibody with an aqueous solution,
    wherein the aqueous solution comprises a buffer, a stabilizer, a surfactant, and a sorbitol tonicifier, and the buffer is an acetate buffer; and
    wherein the anti-interleukin-6 receptor antibody is 5 mg/ml to 30 mg/ml of Tocilizumab IgG; the protein stabilizer is 4% (w/v) to 7% (w/v) of sucrose; the surfactant is 0.01% (w/v) to 0.05% (w/v) of polysorbate 80; the buffer is 10 mM to 30 mM of acetate buffer; and the antibody-containing aqueous formulation has a pH ranging between 5.0 and 6.0.

8. The method of suppressing aggregate formation of claim 7, wherein said sorbitol tonicifier is 1% (w/v) to 4% (w/v).

9. The method of suppressing aggregate formation of claim 7, wherein said antibody-containing aqueous formulation is administered to a subject by intravenous injection or infusion.

10. The method of suppressing aggregate formation of claim 7, wherein the antibody-containing aqueous formulation forms less than 5% of aggregates of the anti-interleukin-6 receptor antibody after 3 months of storage at 40° C.

11. The method of suppressing aggregate formation of claim 7, wherein at least 90% of the anti-interleukin-6 receptor antibody in the antibody-containing aqueous formulation is in monomer form after 3 months of storage at 40° C.

12. The method of suppressing aggregate formation of claim 7, wherein the antibody-containing aqueous formulation forms less than 5% of aggregates and at least 90% of the anti-interleukin-6 receptor antibody in the antibody-containing aqueous formulation is in monomer form after 3 months of storage at 40° C.

* * * * *